United States Patent [19]

Winslow, Jr. et al.

[11] 4,328,366

[45] May 4, 1982

[54] TREATMENT OF WASTE STREAM FROM PENTAERYTHRITOL PRODUCTION

[75] Inventors: Charles E. Winslow, Jr., Norfolk; Leonard C. Ellis, Chesapeake, both of Va.

[73] Assignee: Virginia Chemicals Inc., Portsmouth, Va.

[21] Appl. No.: 124,650

[22] Filed: Feb. 25, 1980

[51] Int. Cl.$^3$ .................. C07C 51/48; C07C 53/06; C07C 29/86; C07C 31/24
[52] U.S. Cl. ........................... 562/513; 203/91; 562/609; 564/462; 564/463; 564/497; 568/853; 568/854
[58] Field of Search ............. 562/513, 609; 568/854, 568/853; 564/497; 203/91

[56] References Cited

U.S. PATENT DOCUMENTS 3,179,704  4/1965  Leonard .................. 562/609

FOREIGN PATENT DOCUMENTS 45-4483   2/1970  Japan ..................... 562/609
52-15566  4/1977  Japan ..................... 562/609

*Primary Examiner*—Vivian Garner
*Attorney, Agent, or Firm*—Depaoli & O'Brien

[57] ABSTRACT

This invention provides a process for recovery of sodium formate from an aqueous waste stream which is a byproduct mother liquor derived from a reaction system in which pentaerythritol is produced by the reaction of formaldehyde with acetaldehyde in the presence of sodium hydroxide catalyst.

As one of its important features, the invention process involves contacting the mother liquor with a monoalkylamine solvent which is highly selective for extraction of organic materials to the exclusion of sodium formate.

31 Claims, No Drawings

TREATMENT OF WASTE STREAM FROM PENTAERYTHRITOL PRODUCTION

BACKGROUND OF THE INVENTION

In an important industrial process for producing pentaerythritol, formaldehyde is reacted with acetaldehyde in the presence of sodium hydroxide catalyst, and the main bulk of pentaerythritol product is recovered from the aqueous reaction medium by crystallization. Typical pentaerythritol processes are described in U.S. Pat. Nos. 2,790,836 and 3,968,176.

The aqueous mother liquor resulting from the manufacture of pentaerythritol is a waste byproduct stream containing sodium formate and unrecovered pentaerythritol, and soluble organic byproduct materials formed in the pentaerythritol synthesizing reaction. This stream represents a difficult waste disposal problem, even though it contains sodium formate of substantial commercial value. If it is attempted to recover the sodium formate by conventional evaporative crystallization means, the presence of the water-soluble organic materials interferes with and impedes this recovery. Because the organics materials become concentrated in the crystallization mother liquor, it becomes quite viscous, thereby hampering crystal separation from the liquor and causing contamination of the separated crystals. In practice, the recovery of sodium formate from the liquor is limited to only 75% of the total sodium formate present, owing to these factors. As a result, a substantial quantity of viscous organic-rich material is produced as a byproduct, which still poses a formidable waste disposal problem.

The potential for recovery of valuable byproducts contained in the aqueous waste stream of a pentaerythritol manufacturing operation has invited various developments which have been reported in the prior art literature.

U.S. Pat. No. 2,441,602 describes an aqueous waste stream treatment method which involves concentrating the stream by water removal, diluting the concentrated stream with a water-soluble monohydric alcohol and heating the diluted mixture, then separating the undissolved metal formate by filtration, distilling the filtrate solution to remove most of the water as an azeotrope with the alcohol, and subsequently cooling the solution to produce crystallized metal formate and pentaerythritol.

U.S. Pat. No. 2,617,791 describes a process for treating pentaerythritol mother liquor which involves heating the mother liquor with a fatty acid at 175°–275° C. until an oily phase and a solids phase are formed, and thereafter recovering the oily layer which contains fatty acid esters of the polyhydroxy compounds.

U.S. Pat. No. 2,780,655 describes a method of treating pentaerythritol mother liquor which involves concentrating the mother liquor to form a slurry of solid pentaerythritol and metal salts, adding formalin to the slurry to dissolve the pentaerythritol, and recovering the undissolved metal salts.

U.S. Pat. No. 3,179,704 describes a method of treating pentaerythritol mother liquor which involves evaporating the mother liquor to dryness, admixing the resulting dried solids with dimethylformamide to dissolve the organic materials, and separating the extract solution from the undissolved formate salts.

U.S. Pat. No. 3,766,277 describes a method of treating an aqueous solution containing pentaerythritol and metal alkanoate which involves contacting the solution with tertiary-butyl alcohol to extract pentaerythritol, and thereafter recovering pentaerythritol by crystallization from the solvent phase.

Other United States patents of general interest relating to the production and recovery of pentaerythritol and various byproducts include U.S. Pat. Nos. 2,004,010; 2,223,421; 2,270,839; 2,386;289; 2,696;507; 2,719,867; 2,782,918; 2,790,011; 2,790,836; 2,790,837; 2,820,066; 3,379,624; 3,478,115; 3,875,248; 3,968,176; 4,083,931; and reference cited therein.

Because of environmental and economic considerations, as indicated by the prior art references disclosed above, there has been continuing investigative effort to develop methods for recovering the valuable organic and inorganic components of waste byproduct streams such as that associated with pentaerythritol production.

Accordingly, it is a main object of the present invention to provide an improved process for recovering organic and inorganic values from the aqueous waste stream derived from pentaerythritol manufacture.

It is another object of this invention to provide a process for treating a pentaerythritol production waste mother liquor which includes a selective extraction step for separating organic components from inorganic components.

It is another object of this invention to provide an immiscible organic solvent which is highly selected for the extraction of pentaerythritol and other organic materials, to the substantial exclusion of sodium formate, as present in a pentaerythritol production aqueous byproduct stream.

It is a further object of this invention to provide a method of recovering in high purity form substantially all of the metal formate contained in an aqueous waste stream derived from pentaerythritol production, in which production formaldehyde is reacted with acetaldehyde in the presence of a metal hydroxide catalyst.

Other objects and advantages of the present invention shall become apparent from the accompanying description and examples.

DESCRIPTION OF THE INVENTION

As noted previously, a commercial method of producing pentaerythritol involves the reaction of formaldehyde with acetaldehyde in the presence of a metal hydroxide catalyst. The resultant reaction product mixture is cooled to effect the separation of a major proportion of pentaerythritol component as a crystalline solid. After the crystalline solid phase is isolated by a conventional solid-liquid separation means, the mother liquor is removed from the reaction system and handled as a waste byproduct stream.

In the case where sodium hydroxide is the catalyst, a typical waste byproduct stream nominally corresponds to the following weight percent composition:

| | |
|---|---|
| Sodium Formate | 28.3% |
| Sodium Sulfate | 0.3% |
| Pentaerythritol | 5.4% |
| Other Organics | 7.5% |
| Water | 58.5% |

The total organic content of the waste stream usually will average in the range of about 10–20 weight percent. The organic components are primarily water-soluble polyhydroxy compounds such as pentaerythritol, formals, sugars, and the like.

The present invention process is adapted to improve the material balance associated with the separation and recovery of metal formate and other byproduct components which are contained in the said aqueous byproduct stream of a pentaerythritol manufacturing operation.

Thus, one or more objects of the present invention are accomplished by the provision of a process for recovery of metal formate from an aqueous waste stream, which aqueous waste stream is a byproduct stream derived from a reaction system in which pentaerythritol is produced by the reaction of formaldehyde with acetaldehyde in the presence of metal hydroxide catalyst and the pentaerythritol product is recovered from the aqueous reaction medium by crystallization, wherein the process comprises the steps of (1) contacting and extracting the said aqueous waste stream with an immiscible alkylamine solvent; (2) separating the formed immiscible organic solvent phase from the aqueous phase; (3) concentrating the said aqueous phase by water removal to precipitate metal formate; and (4) separating and recovering the precipitated metal formate from the aqueous medium.

By the term "metal" as employed herein with reference to formates and hydroxides is meant alkali and alkaline earth metals.

In a preferred embodiment, this invention provides a process for recovery of sodium formate from an aqueous waste stream, which aqueous waste stream is a byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) contacting and extracting the said aqueous waste stream with an immiscible monoalkylamine solvent; (2) separating the formed immiscible organic solvent phase from the aqueous phase; (3) concentrating the said aqueous phase by water removal to precipitate sodium formate; and (4) separating and recovering the precipitated sodium formate from the aqueous medium.

In another preferred embodiment, this invention provides a process for recovery of sodium formate from an aqueous waste stream, which aqueous waste stream is a byproduct stream derived from a reaction system in which pentaerythritol is produced by the reaction of formaldehyde with acetaldehyde in the presence of sodium hydroxide catalyst and the pentaerythritol product is removed from the aqueous reaction medium by crystallization, wherein the process comprises the steps of (1) contacting and extracting the said aqueous waste stream with an immiscible monoalkylamine solvent; (2) separating the formed immiscible organic solvent phase from the aqueous phase; (3) concentrating the said aqueous phase by water removal to precipitate sodium formate; (4) separating and recovering the precipitated sodium formate from the aqueous medium; and (5) evaporating the said organic solvent phase to recover monoalkylamine solvent and pentaerythritol and other organic components as separate fractions.

In a further preferred embodiment, this invention provides a process for recovery of sodium formate from an aqueous waste stream, which aqueous waste stream is a byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) admixing the aqueous waste stream feed with a quantity of ammonia or low molecular weight amine which is sufficient to react with all of the waste stream components which are reactive with ammonia; or amine; (2) contacting and extracting the treated aqueous waste stream feed with an immiscible monoalkylamine solvent; (3) separating the formed immiscible organic solvent phase from the aqueous phase; (4) concentrating the said aqueous phase by water removal to precipitate sodium formate; and (5) separating and recovering the precipitated sodium formate from the aqueous medium.

By the term "immiscible" solvent as employed herein is meant an amine solvent which is substantially immiscible in the aqueous waste stream being treated.

The term "monoalkylamine" as employed herein is meant to include substantially immiscible organic compounds corresponding to the formula:

$$R-NH_2$$

where R is preferably selected from alkyl and cycloalkyl substituents containing between about 4–12 carbon atoms. Illustrative of alkyl substituents are n-butyl, isobutyl, n-pentyl, isopentyl, n-hexyl, 1-methylhexyl, 2-ethylhexyl, cyclohexyl, n-octyl, n-decyl, and the like.

For purposes of the present invention, a monoalkylamine solvent as defined above meets the following performance criteria:

(1) The solvent extracts a high percentage of the organic components in a minimal number of extraction stages while employing a minimal quantity of solvent;

(2) The solvent extracts a very low percentage of the metal formate present in the waste stream;

(3) The solvent is essentially insoluble in the waste stream so that very little is lost in the aqueous stream exiting the extraction process; and (4) The solvent is readily separable from the extracted organic components so that the solvent can be recovered with minimal expense for recycle to the extraction step.

If desired, a dialkylamine solvent can be employed instead of the more preferred monoalkylamine solvent. Illustrative of dialkylamine solvents are immiscible alkylamines containing between about 4–12 carbon atoms such as dipropylamine, dibutylamine, dicyclohexylamine, and the like.

Also, although much less satisfactory than a monoalkylamine or dialkylamine solvent, other amine compounds may be employed such as aliphatic, alicyclic and aromatic mono-, di, and tri-substituted immiscible amine compounds containing a total of between about 4–12 carbon atoms, e.g., 6-hydroxyhexylamine; tripropylamine; 4-piperidylamine; tri(2-chloroethyl)amine; dimethylphenylamine; and the like.

In the step (1) solvent extraction procedure recited above, the immiscible amine solvent is employed in a quantity between about 0.5–5 volumes, and preferably between about 0.8–2 volumes, per volume of the said aqueous waste stream.

The step (1) extraction procedure is conducted at a temperature in the range between about 5°–60° C., and preferably at a temperature in the range between about 10°–40° C. Higher temperatures tend to lower the efficiency of the extraction, for example, by adversely affecting the selective partitioning of components between the immiscible solvent and aqueous phases.

An important aspect of the step (1) extracting procedure is the achievement of efficient contacting between the solvent and aqueous phases. In a batch operation, the intimate contacting of phases can be accomplished by high speed stirring. In a continuous operation, the contacting of phases can be accomplished in a conventional countercurrent extraction column.

A suitable contacting time between the solvent and aqueous phases will vary in the range between about 10 seconds and 30 minutes, depending on the particular amine solvent employed, the volumes of the liquid phases, the temperature of the extraction zone, and other such determining factors.

After the period of efficient contacting between the solvent and aqueous phases is completed, the two phases are allowed to separate out into distinct layers, preferably at a temperature between about 10°–40° C. When a solvent such as 2-ethylhexylamine is employed, the phase separation occurs rapidly, e.g., in a time period between about 1–10 minutes.

After the solvent and aqueous phases are recovered as separate fractions, each fraction is subjected to further separation procedures.

The volume of the aqueous phase is concentrated by water removal, preferably by vacuum evaporation, so as to cause precipitation of metal formate solute as a crystalline solid. The metal formate precipitate is isolated by decantation or centrifugation or filtration. A high purity metal formate (e.g., sodium formate) is obtained in a quantity which represents as much as 99 weight percent of the metal formate which was contained in the original waste stream feed.

The organic phae which is recovered as a separate fraction in a manner as described above is charged to a distillation or evaporation unit, and the amine solvent is stripped from the mixture. The residual fraction from the distillation or evaporation is substantially heavy organic material which has fuel value suitable for steam generation.

As noted previously hereinabove, a particularly important embodiment of the present invention involves the pretreatment of the original aqueous waste stream feed with ammonia or low molecular weight amine before the solvent extraction step. As demonstrated in Example IV below, ammonia or a lower amine is reactive with certain of the components in the aqueous feed (e.g., carbonyl compounds). The interaction between the ammonia or amine and the reactive species serves to consume the reactive sites, which otherwise would react with the more valuable amine solvent. Hence, the ammonia or amine pretreatment reduces the loss of amine solvent in the subsequent processing stages. The ammonia or amine pretreatment proceeds rapidly when the ammonia or amine is incorporated into the aqueous feed at ambient temperatures. The ammonia or amine is employed in a quantity which is at least sufficient to consume all of the sites which are reactive with ammonia or amine under the contacting conditions.

Illustrative of reactive low molecular weight amines are methylamine, dimethylamine, ethylamine, diethylamine, ethyleneimine, ethylenediamine, and the like.

The following examples are further illustrative of the present invention. The reactants and other specific ingredients are presented as being typical, and various modifications can be derived in view of the foregoing disclosure within the scope of the invention.

EXAMPLE I

This example illustrates the unique properties of immiscible amine solvents for selective extraction of water-soluble organic components, with the substantial exclusion of sodium formate, from an aqueous waste stream derived from a pentaerythritol plant.

The comparative solvent extraction runs respectively were conducted at room temperature as a four-stage counter-current procedure in a series of separatory funnels. A 1:1 volume of solvent to aqueous feed was employed.

| Solvent | Weight % Organic Material Extracted |
|---|---|
| di-n-propylamine | 40 |
| n-butylamine | 85 |
| di-n-butylamine | 21 |
| tri-n-butylamine | 2 |
| diamylamine | 6 |
| cyclohexylamine | 80 |
| 2-ethylhexylamine | 88 |

The 2-ethylhexylamine solvent extracted about 1% of the sodium formate contained in the aqueous feed under the extraction conditions. The n-butylamine solvent extracted about 22% of the said sodium formate content of the feed.

The above results demonstrated that an immiscible amine solvent unexpectedly is highly selective for extracting water-soluble organic compounds from an aqueous medium, with the substantial exclusion of sodium formate. 2-Ethylhexylamine is particularly outstanding in this regard, even when compared with dialkylamine and other amine solvents.

Organic solvents found to be unsuitable for purposes of the present invention include n-butyl alcohol, isobutanol, octyl alcohol, 2-(dibutylamino)ethanol, 2-(diisopropylamine)ethanol, ethyl acetate, and methyl isobutyl ketone.

EXAMPLE II

In a manner similar to that in Example I, a five-stage countercurrent extraction was conducted employing 250 ml separatory funnels. The aqueous phase feed to each cycle was 100 ml (123.2 gm) containing 34.9 gm of sodium formate and 15.9 gm of water-soluble organic material. The solvent feed to each cycle was also 100 ml (78.0 gm) of 2-ethylhexylamine. All extractions were performed at room temperture.

The extract phase resulting from these operations was found to contain only 0.3 gm of sodium formate, while the extracted aqueous phase (raffinate) contained only 1.1 gm of organic material. This represented an extraction of 93% of the organic material and less than 1% of the sodium formate.

EXAMPLE III

The extraction phase of the invention process was conducted in a continuous countercurrent extraction column. The unit had a three-inch inside diameter and 5.5 feet of active height, and was equivalent to 1.4 theoretical extraction stages.

In conjunction with the extraction phase, a continuous vacuum evaporation unit was employed for recovery of the 2-ethylhexylamine solvent from the extract medium. The recovered solvent was recycled in the process.

A total of 1753.4 lbs. of aqueous waste stream were fed to the extractor along with 1351.5 lbs. of 2-ethylhexylamine as solvent. The compositions of these streams were as shown in the table below. The unit was operated at 40°±2° C.

The resultant immiscible phases constituted 1623.5 lbs. of raffinate and 1484.0 lbs. of extract. The compositions of these streams were as shown in the table below. It is to be noted that 132.2 lbs. of material were transferred from the aqueous phase to the solvent phase. Of the 132.2 lbs. transferred, 4.3 lbs. were sodium formate, 6.0 lbs. were water, and the remaining 122.0 lbs. were organic materials. This represented an extraction of 72% of the organic material in the feed and only 0.88% of the sodium formate.

Calculations indicated that 0.5 lb. of 2-ethyhexylamine was lost in the raffinate. Evaporation of the extract phase regenerated the 2-ethylhexylamine for reuse. The organic residue left after evaporation of the 2-ethylhexylamine was found to contain 0.6% of 2-ethylhexylamine, which represented a further loss of solvent of 0.8 lb.

This organic residue should have weighed 127.1 lbs., the sum of the organic material and sodium formate extracted, plus the residual 0.8 lb. of 2-ethylhexylamine. Instead, its weight was found to be 137.7 lbs., or 10.6 lbs. in excess of that expected.

The recovery of 2-ethylhexylamine was approximately 10 lbs. less than calculated. While this quantity was only 0.8% of the 2-ethylhexylamine fed to the extraction, its loss adversely affected the economics of the process. Further analytical work determined that the missing 2-ethylhexylamine was incorporated in the organic residue as a chemically bound species not identifiable as an amine.

| | Stream Compositions (Weight Percent) | | | |
|---|---|---|---|---|
| | Sodium Formate | Organic Material | Water | 2-Ethyl-hexylamine |
| Aqueous Feed | 27.6 | 10.0 | 62.4 | 0.0 |
| Solvent Feed | 0.0 | 0.0 | 8.6 | 91.4 |
| Raffinate | 29.5 | 3.3 | 67.2 | 0.03 |
| Extract | 0.3 | 8.2 | 8.1 | 83.4 |

As further illustrated in the following Example IV, the loss of 2-ethylhexylamine via reaction with some component of the aqueous stream as described above, involved the reaction of 6.1 lbs. or 0.047 mol of 2-ethylhexylamine per 100 lbs. of organic material contained in the aqueous feed stream. It was found that ammonia in this same molar amount, i.e., 0.047 mol or 0.8 lb. of ammonia per 100 lbs. of organic material, can react with the reactive species in the aqueous waste stream prior to entering the extraction process. In this way the reactive sites can be consumed by an inexpensive, low molecular weight chemical (e.g., ammonia or low molecular weight amine such as methylamine), so that the more expensive, high molecular weight solvent (e.g., 2-ethylhexylamine) is not consumed via chemical reaction during the extraction process.

EXAMPLE IV

This example illustrates the improved material balance which is achieved when the aqueous waste stream feed is pretreated with ammonia prior to the extraction step of the invention process.

To 637.0 lbs. of aqueous waste stream there was added 0.5 lb. of ammonia. The mixture was well agitated at room temperature and then fed to the extraction column along with 454.8 lbs. of 2-ethylhexylamine as the extraction solvent. The compositions of these streams were as shown in the table below. Operation of the unit was at 40°±2° C.

About 584.2 lbs. of raffinate and 508 lbs. of extract phases were produced. The compositions of these streams were as shown in the table below. About 53.3 lbs. of material were transferred from the aqueous phase to the solvent phase. Of the 53.3 lbs. transferred, 1.5 lbs. were sodium formate, 2.1 lbs. were water, and the remaining 49.7 lbs. were organic materials. This represents an extraction of 74% of the organic material in the feed and 0.83% of the sodium formate. Calculations indicated that only 0.21 lb. of 2-ethylhexylamine was lost in the raffinate. Regeneration of the 2-ethylhexylamine via vacuum evaporation generated an organic residue containing 0.6% of 2-ethylhexylamine, corresponding to 0.3 lb. of that solvent.

This organic residue should have weighed 51.5 lbs., the sum of the organic material and sodium formate extracted, plus the residual 0.3 lb. of 2-ethylhexylamine. Instead, its weight was found to be 50.8 lbs., leaving an unknown loss of 0.7 lb., but indicating that no chemically reacted 2-ethylhexylamine was incorporated in the organic residue. More significantly, the recovery of 2-ethylhexylamine from the evaporation was essentially 100% of that expected.

| | Stream Compositions (Weight Percent) | | | |
|---|---|---|---|---|
| | Sodium Formate | Organic Material | Water | 2-Ethyl-hexylamine |
| Aqueous Feed | 28.2 | 10.6 | 61.2 | 0.0 |
| Solvent Feed | 0.0 | 0.0 | 8.8 | 91.2 |
| Raffinate | 30.6 | 3.0 | 66.4 | 0.03 |
| Extract | 0.3 | 9.8 | 8.3 | 81.6 |

What is claimed is:

1. A process for recovery of alkali and alkaline earth metal formates from an aqueous waste stream, which aqueous waste stream is a byproduct stream derived from a reaction system in which pentaerythritol is produced by the reaction of formaldehyde with acetaldehyde in the presence of alkali and alkaline earth metal hydroxide catalysts and the pentaerythritol product is recovered from the aqueous reaction medium by crystallization, wherein the process comprises the steps if (1) contacting and extracting said aqueous waste stream with an immiscible amine solvent; (2) separating the formed immiscible organic solvent phase from the aqueous phase; (3) concentrating said aqueous phase by water removal to precipitate said alkali and alkaline earth metal formates; and (4) separating and recovering the precipitated alkali and alkaline earth metal formates from the aqueous medium.

2. A process in accordance with claim 1 wherein said amine solvent in step (1) corresponds to the formula:

R—NH$_2$ where R is selected from the group consisting of alkyl and cycloalkyl substituents containing between four and about twelve carbon atoms.

3. A process in accordance with claim 1 wherein the amine solvent in step (1) contains between four and about twelve carbon atoms.

4. A process in accordance with claim 3 wherein the amine solvent is dipropylamine.

5. A process in accordance with claim 3 wherein the amine solvent is dibutylamine.

6. A process in accordance with claim 3 wherein the amine solvent is dicyclohexylamine.

7. A process for recovery of sodium formate from an aqueous waste stream, which aqueous waste stream is a byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) contacting and extracting said aqueous waste stream with an immiscible amine solvent; (2) separating the formed immiscible organic solvent phase from the aqueous phase; (3) concentrating said aqueous phase by water removal to precipitate sodium formate; and (4) separating and recovering the precipitated sodium formate from the aqueous medium.

8. A process in accordance with claim 7 wherein the amine solvent in step (1) is employed in a quantity between about 0.5–5 volumes of solvent per volume of aqueous waste stream.

9. A process in accordance with claim 7 wherein the step (1) contacting and extracting operation is conducted as a countercurrent procedure.

10. A process in accordance with claim 7 wherein the step (1) contacting and extracting operation is conducted at a temperature in the range between about 10°–40° C.

11. A process in accordance with claim 7 wherein the step (2) separating of immiscible phases is conducted at a temperature between about 10°–40° C.

12. A process in accordance with claim 7 wherein the step (3) concentrating and water removal is accomplished by vacuum evaporation.

13. A process in accordance with claim 7 wherein said amine solvent in step (1) corresponds to the formula:

$$R-NH_2$$

where R is selected from the group consisting of alkyl and cycloalkyl substituents containing between four and about twelve carbon atoms.

14. A process in accordance with claim 13 wherein the amine solvent is n-butylamine.

15. A process in accordance with claim 13 wherein the amine solvent is n-pentylamine.

16. A process in accordance with claim 13 wherein the amine solvent is n-hexylamine.

17. A process in accordance with claim 13 wherein the amine solvent is cyclohexylamine.

18. A process in accordance with claim 13 wherein amine solvent is 2-ethylhexylamine.

19. A process in accordance with claim 13 wherein the amine solvent is n-decylamine.

20. A process for recovery of sodium formate from an aqueous waste stream, which aqueous waste stream is a byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) contacting and extracting said aqueous waste stream with an immiscible amine solvent; (2) separating the formed immiscible organic solvent phase from the aqueous phase; (3) concentrating said aqueous phase by water removal to precipitate sodium formate; (4) separating and recovering the precipitated sodium formate from the aqueous medium; and (5) evaporating said organic solvent phase to recover said amine solvent and pentaerythritol and other organic components as separate fractions.

21. A process in accordance with claim 20 wherein amine solvent recovered in step (5) is recycled to step (1) of the process.

22. A process for recovery of sodium formate from an aqueous waste stream, which aqueous waste stream is a byproduct stream derived from a reaction system in which pentaerythritol is produced by the reaction of formaldehyde with acetaldehyde in the presence of sodium hydroxide catalyst and the pentaerythritol product is recovered from the aqueous reaction medium by crystallization, wherein the process comprises the steps of (1) admixing the aqueous waste stream feed with a quantity of ammonia or a low molecular weight amine which is sufficient to react with all of the waste stream components which are reactive with said ammonia or said amine; (2) contacting and extracting the treated aqueous waste stream feed with an immiscible amine solvent; (3) separating the formed immiscible organic solvent phase from the aqueous phase; (4) concentrating said aqueous phase by water removal to precipitate sodium formate; and (5) separating and recovering the precipitated sodium formate from the aqueous medium.

23. A process in accordance with claim 22 wherein the low molecular weight amine in step (1) is methylamine.

24. A process in accordance with claim 22 wherein the low molecular weight amine in step (1) is ethylenediamine.

25. A process in accordance with claim 22 wherein the amine solvent in step (2) is 2-ethylhexylamine.

26. A process in accordance with claim 22 wherein said amine solvent in step (2) corresponds to the formula:

$$R-NH_2$$

where R is selected from the group consisting of alkyl and cycloalkyl substituents containing between four and about twelve carbon atoms.

27. A process in accordance with claim 22 wherein the amine solvent in step (2) is n-butylamine.

28. A process in accordance with claim 22 wherein the amine solvent in step (2) is n-pentylamine.

29. A process in accordance with claim 22 wherein the amine solvent in step 2 is n-hexylamine.

30. A process in accordance with claim 22 wherein the amine solvent in step (2) is cyclohexylamine.

31. A process in accordance with claim 22 wherein the amine solvent in step (2) is n-decylamine.

* * * * *